(12) United States Patent
Swartz

(10) Patent No.: US 7,564,979 B2
(45) Date of Patent: Jul. 21, 2009

(54) LISTENER SPECIFIC AUDIO REPRODUCTION SYSTEM

(76) Inventor: Robert Swartz, 349 Marsham Ave., Highland Park, IL (US) 60035-4734

( * ) Notice: Subject to any disclaimer, the term of this patent is extended or adjusted under 35 U.S.C. 154(b) by 1107 days.

(21) Appl. No.: 11/032,367

(22) Filed: Jan. 8, 2005

(65) Prior Publication Data
US 2005/0094822 A1    May 5, 2005

(51) Int. Cl.
*H04R 25/00*    (2006.01)
(52) U.S. Cl. .......................................... 381/60; 381/312
(58) Field of Classification Search .................. 381/56, 381/58, 60, 312, 314, 315, 320, 321, 71.6, 381/104; 600/559; 73/585
See application file for complete search history.

(56) References Cited

U.S. PATENT DOCUMENTS 5,604,812 A * 2/1997 Meyer ........................ 381/314
5,666,424 A * 9/1997 Fosgate et al. ................ 381/18
6,035,050 A * 3/2000 Weinfurtner et al. ........ 381/313
6,094,489 A * 7/2000 Ishige et al. .................. 381/60
6,118,877 A * 9/2000 Lindemann et al. ........... 381/60

\* cited by examiner

*Primary Examiner*—Huyen D Le

(57) ABSTRACT

A system for use with an audio reproduction system that corrects for distortion caused by the system as well as any hearing impairment suffered a listener. Test signals are introduced into the input of the system to produce test sounds that are perceptible by the listener. Using a pushbutton, the listener indicates when a test signal of progressively increasing volume reaches an audible level. The resulting measured values of the listener's threshold of hearing at different frequencies is compared with comparable data for a normal listener to generate correction values that are used to program an equalizer which compensates for not only the listener's hearing impairments but also any distortion produced by system components or room acoustics.

14 Claims, 4 Drawing Sheets

LISTENER SPECIFIC AUDIO REPRODUCTION SYSTEM

FIELD OF THE INVENTION

This invention relates to audio reproduction systems and more particularly to reproduction systems which incorporate methods and apparatus for compensating for the listener's hearing impairments.

BACKGROUND OF THE INVENTION

It is typically the goal of electronic reproduction equipment to reproduced sound waves that accurate replicate original sound waves picked up by microphone. Although modern electronic amplifiers that are highly linear across the audible frequency range are now available at low cost, microphones and speakers or headsets differ significantly in their ability to faithfully transform sound waves into electrical signals and back again across the audible spectrum. In addition, room acoustics often cause more degradation in the quality of reproduced sound reproduction than the system components used.

In order to compensate for these and other variations, sound systems commonly include adjustable mechanisms which vary from simple "tone controls" to elaborate "graphical equalizers" that may be manually adjusted by the user to obtain a desired sound quality. In addition, a number of commercially available advanced stereo systems employ automated mechanisms that sample the sound produced by the combination of speakers and room acoustics and then modify relative gain of different channels to compensate for the characteristics of the speakers and the room acoustics. These automated balancing systems are widely used for adjusting the relative magnitude of sound produced by multiple speakers in a "surround sound" system. For example, U.S. Pat. No. 5,666,424 issued to Fosgate et al. on Sep. 9, 1997 describes a surround sound system that employs a microprocessor to digitally control the gain of each channel. The microprocessor receives an input signal from a microphone placed at the preferred listening location within the listening area for automatically balancing the relative channel gains during a calibration process to yield the best possible surround sound reproduction of the stereophonic source material. As a visual aid, the microprocessor displays menus and messages on a video screen, and a visual display shows the relative levels of the six axes of control signals within the surround sound processor.

These automatic calibration systems do not compensate for differences in the hearing abilities of different listeners. Everyone's hearing has a different response to sound. Those with normal healthy hearing perceive sounds at the low and high ends of the audible frequency range at greatly reduced volume. Genetic causes, certain diseases, and exposure to loud noises can further impair hearing in different ways. And as we age, our ability to hear high and low frequencies is reduced even more. The nature and extent of these degradations is different for every individual and, as a result, the sounds we hear, whether "live" or reproduced, are a distorted version of the actual sound pressure waves that reach our ears.

To help restore normal hearing, hearing aids are available that use adjustable filtering and automatic gain control (AGC) parameters. Since given individual's hearing loss is typically not uniform over the entire frequency spectrum of audible sound, with the loss often being greater at higher frequency ranges than at lower frequencies, it has become common for a hearing health professional to make audiological measurements that will indicate the type of correction or assistance that will be the most beneficial to improve that individual's hearing capability.

Various systems for measuring auditory responses are known. These systems usually provide for application of selected tones, broad-band noise, and/or narrow-band noise which is variable in frequency and amplitude to aid in determining the amount of hearing loss a person may have. To assess hearing thresholds for speech, an audiometer may also reproduce live voice or recorded speech at selectable calibrated levels. Various controls are used to administer varying sound conditions to determine a range of responses for the individual. The audiological data which records the individual's hearing response are typically charted or graphed, and these charts are then used as the basis for adjusting the gain vs. frequency characteristics of a programmable hearing aid so that it can better compensate for the hearing loss characteristics of the wearer.

U.S. Pat. No. 5,604,812 issued to Meyer on Feb. 18, 1997 entitled "Programmable hearing aid with automatic adaption to auditory conditions" and the prior art patents cited therein describe hearing aids that can be programmed by the wearer. The hearing-impaired person can retrieve a test program of test tones stored a memory in the hearing aid and can actuate a switch when the desired (appropriate) hearing threshold is reached, and thus store a correction factor each test tone. These stored correction factors adust the signal transfer characteristics of the hearing aid and are retained until the wearer again reprograms the hearing aid in the same way. U.S. Pat. No. 6,035,050 issued to Weinfurtner et al. on Mar. 7, 2000 describes a further "Programmable hearing aid system and method for determining optimum parameter sets in a hearing aid."

SUMMARY OF THE INVENTION

It is an object of the present invention to improve the quality of sound delivered by a sound reproduction system as perceived by a person with impaired hearing.

It is a further object of the invention to improve the quality of sound heard by a listener by correcting for distortion introduced by sound reproduction equipment, room acoustics, and any hearing disability suffered by the listener.

It is a still further object of the invention to improve the quality of sound produced by an electronic sound system by using the system to delivering audible test sound stimuli to the listener, accepting responses from said listener indicative of the listener's perception of the test stimuli, translating the listener's responses into measured audiological data characterizing listener's hearing, calculating control values from said measured audiological data, and adjusting a programmable equalizer to preferentially amplify sound delivered to the listener at different frequencies in response to the control values.

A preferred embodiment of the invention takes the form of an automatically programmable distortion correction mechanism that can be used with an electronic sound reproduction system. The reproduction system typically includes an electronic amplifier having an input connected to an audio signal source and an output connected to an electro-acoustical transducer for delivering sound waves to a listener who may have impaired hearing. The programmable correction mechanism employs a test signal source coupled to system input for delivering audible test sound stimuli to the listener by way of one or more speakers or headphones. The mechanism further includes means for accepting responses from said listener that indicate the listener's perception of the test sound stimuli. A processor is used to translate these responses into measured audiological data that characterize the listener's hearing and to calculate equalization control values from the measured audiological data. An equalizer selectively amplifies the sound delivered to the listener at different frequencies in accordance with the calculated control values.

In accordance with a further feature of the invention, the correction mechanism may advantageously store audiometric data indicative of the nominal frequency response characteristics of a person with normal hearing, and the processor may then compare the measured audiological data indicating the current listener's hearing ability with said audiometric data indicating normal hearing ability, and thus produce correction values that produce an output which the listener hears in the same way a normal person would have heard the originally recorded sounds.

The present invention may be implemented at low cost in existing sound systems such as home entertainment systems, television and radio sets, and portable audio players. The invention may be used to particular advantage in portable audio players which use headphones. Such devices typically include the "hardware" needed to implement the principle functions needed (generating test signals of different frequencies and amplitudes, accepting indications from a listener indicating how these test signals are perceived, processing these indications to produce equalization control values, and adjusting the transfer characteristics of the reproduction system), allowing the invention to be incorporated into existing systems merely by adding appropriate control software.

These and other objects, features and advantages of the present invention may be better understood by considering the following detailed description of a preferred embodiment of the invention.

BRIEF DESCRIPTION OF THE DRAWINGS

In the detailed description which follows, frequent reference will be made to the attached drawings, in which.

DETAILED DESCRIPTION

Figure 1:
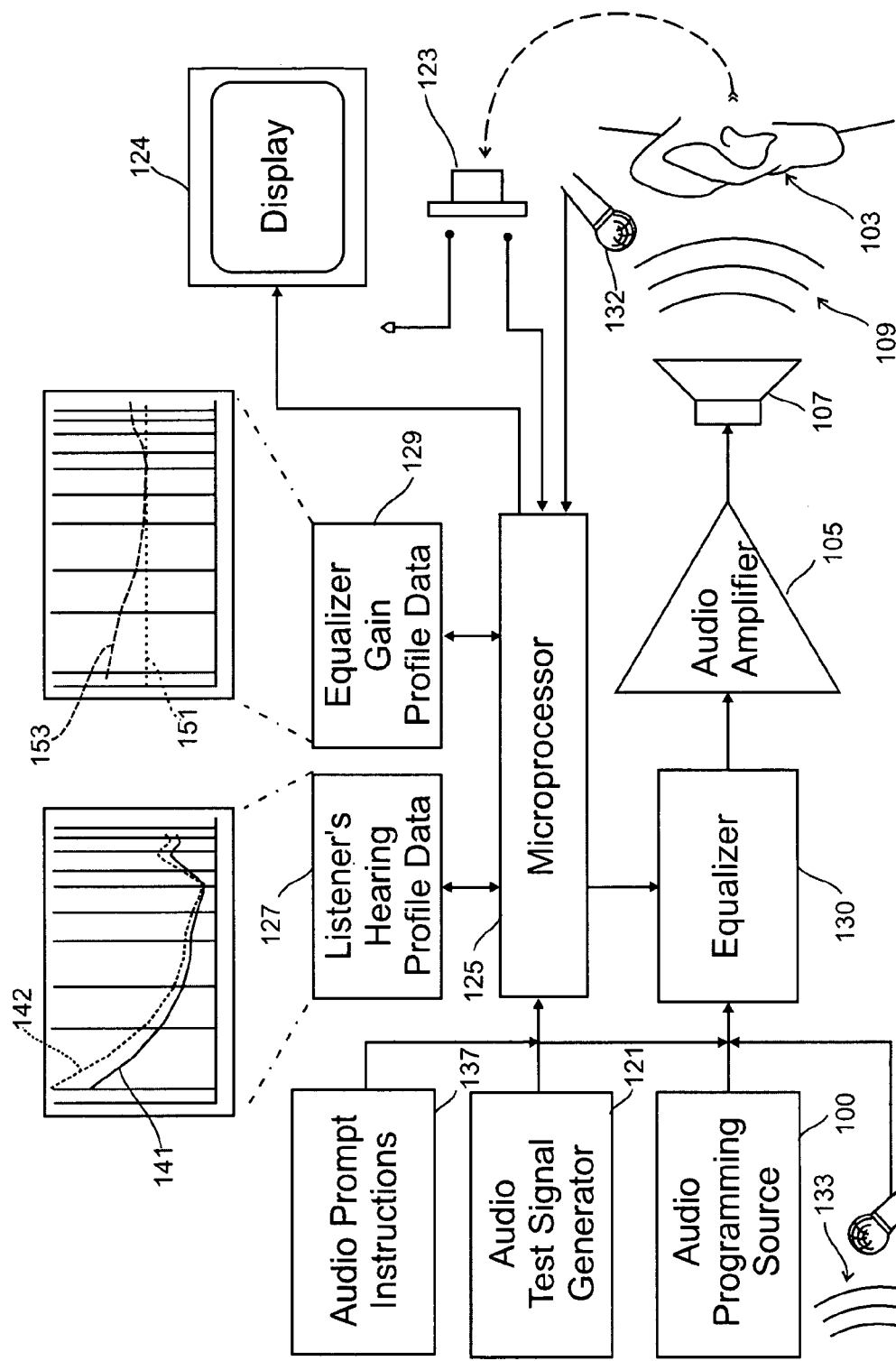
FIG. 1 is schematic block diagram of a sound reproduction system embodying the invention.

A schematic diagram of an illustrative implementation of the invention is shown in FIG. 1. Sound from an electronic audio programming signal source 100 is delivered to a human ear 103 by a sound reproduction system that includes an automatic equalization scheme to compensate for:

(1) defects in the reproduction capabilities of the programming signal source 100 and of an electronic audio amplifier depicted at 105,
(2) distortion introduced by an electrical-to-acoustic transducer illustrated by the loudspeaker seen at 107,
(3) distortion introduced by room acoustics or other sound transmission media which transmit the sound waves 109 to the ear 103, and
(4) defects in the listener's hearing ability.

The mechanism for correcting for distortions caused by the reproduction components, the acoustic transmission medium and the listener's hearing employs a test signal generator 121 for introducing audio test signals into the system, a mechanism illustrated by the pushbutton 123 for accepting indications from the listener that specify the listener's perception of those test signals as reproduced by the available equipment and room conditions, and a microprocessor 125 for storing audiometric data at 127 indicating how the listener perceived different test signals and how normal listeners would perceive those signals. The microprocessor 125 processes this data to produce and store gain control values at 129 which are used to adjust the response characteristics of an electronically adjustable equalizer seen at 130.

The traditional goal of audio reproduction has been the accurate reproduction of the original sound. A mechanism for correcting the reproduction system including an output speaker 107 as illustrated in FIG. 1 can be implemented using two identical microphones seen at 131 and 132. The microphone 131 captures original sound pressure waves 133 from a sound source (not shown) and the microphone 132 captures the reproduced sound 109 from the output speaker 107. As the frequency of the input sound waves 133 changes from the low to the high end of the audible range, the reproduction components should ideally exhibit constant gain (i.e. should have a linear response) over the entire frequency range. By comparing the outputs from microphones 131 and 132, the microprocessor 125 can generate equalizer gain profile data stored at 129 to adjust the frequency response of the programmable equalizer 130 in order to provide the desired linear response over the entire frequency range. In this way, the sound waves at 109 should accurately replicate the original sound waves at 133.

A second automatic equalization scheme could be used that would eliminate the microphone 131. The test signal generator 121 may instead be employed to generate an input test signal which varies in frequency and has constant amplitude of the audio frequency range. As the frequency changes, the amplitude of the output sound may be detected by the microphone 132 and the gain profile of the equalizer 130 may be adjusted so that the amplitude of the signal output of the microphone 132 is constant across the audible frequency range. This approach, however, will not result in truly linear response unless the response of the microphone 132 is linear whereas, using two identical microphones as described earlier, any nonlinear properties of the two identical microphones will cancel out.

Figure 2:
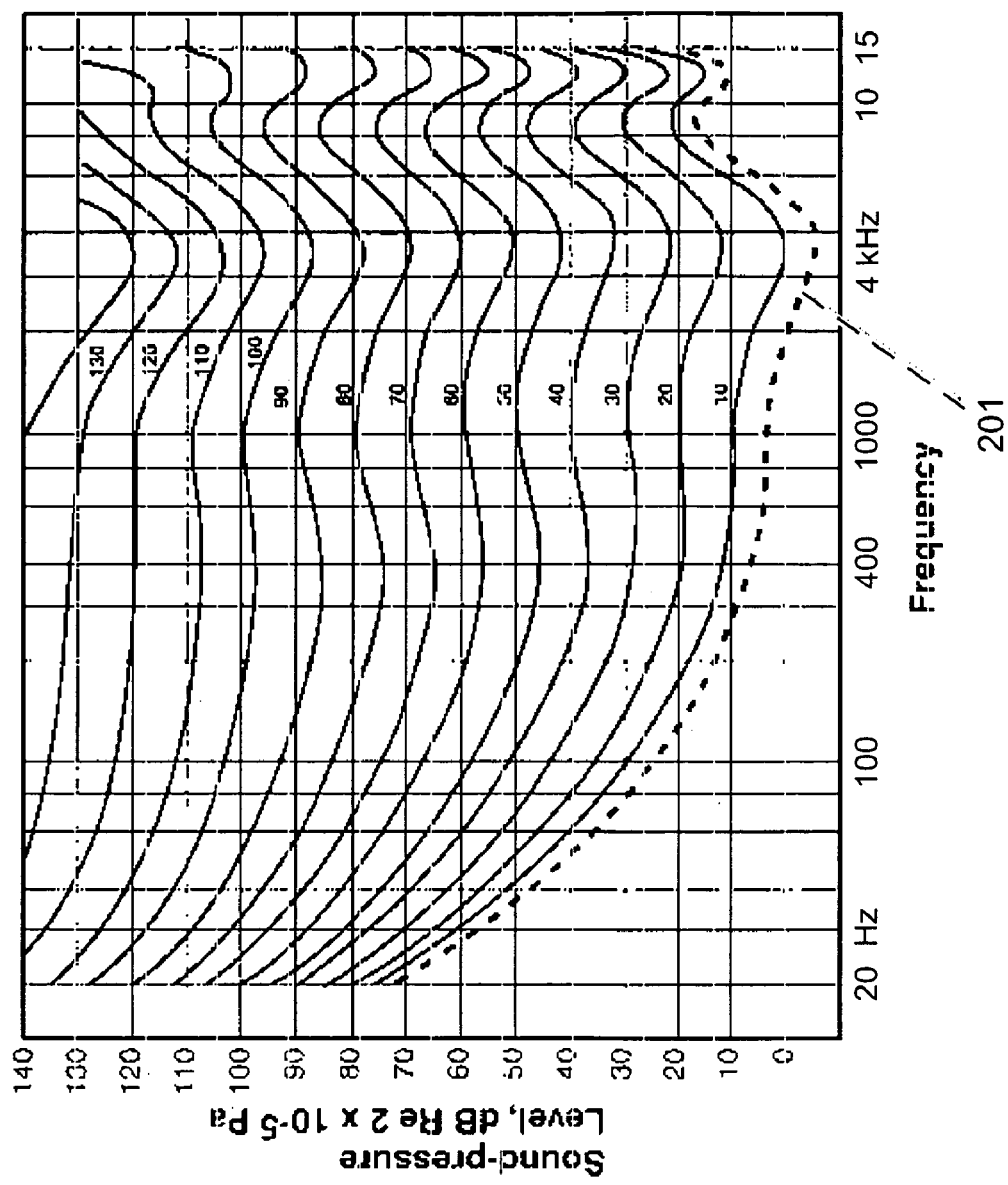
FIG. 2 is a chart showing the measured frequency response of a normal person's hearing.

Improving the sound reproduction capabilities of the components is becoming less important since the quality of sound reproduction has increased steadily over the years. This is especially true of electronic audio sources like CD players, radios, home entertainment systems, television sets, and computer playback equipment which employ solid state amplifiers. Speakers and headphones have also improved significantly. Given the continual improvement of electronic devices, even moderately priced equipment now rivals high end equipment in sound reproduction quality. As a result, the acoustics of the room in which the equipment is used often has a greater effect on the accuracy of the sound reproduction than the electronic amplifiers and speakers. While automatic equalization techniques of the type described above can also correct for poor room acoustics, it cannot compensate for the distortion in the sound heard by the listener because of the listener's impaired hearing ability The human ear is not equally sensitive to all frequencies, and hearing everyone's hearing ability is reduced in the low and high frequency ranges. The average hearing response over the entire audio range as been measured and charted by testing a significant number of people with normal hearing. This work, originally conducted by Fletcher and Munson in 1933, with later refinements by others, has produced a set of curves seen in FIG. 2 which specify the sound pressure levels of tones of different frequencies that are perceived as being equally loud by the average listener. These curves in FIG. 2 are plotted for each 10 dB rise in sound level. The lowest curve, seen as a dashed line 201 in FIG. 2, indicates the "threshold of hearing"—the lowest sound level which is perceptible by the average person at different frequencies over the audio range. The uppermost curve plots sound pressure levels at the "threshold of pain" at which the average person experiences significant discomfort As seen in FIG. 2, all of the curves are lowest in the range from 1 to 5 kHz, with a dip at about 4 kHz, indicating that the ear is most sensitive to frequencies in this range. The intensity of higher or lower frequency tones must be raised substantially in order to create the same impression to the average listener as a 4 kHz tone.

Although it would be possible to provide a human listener with a hearing aid or other sound reproduction system that compensates for the "normal" degradation in hearing ability at high and low frequencies, thereby given the listener a more nearly "linear" hearing capability, so that the listener would perceive sounds of equal sound pressure across the audio range as having the same volume, the result would sound very unnatural. Thus, while sound reproduction equipment should faithfully reproduce the original sound waves and exhibit a linear frequency response, mechanisms which correct hearing defects should restore a person's hearing to a normal response of the kind depicted in FIG. 2 rather than giving the listener a linear response.

Figure 4:
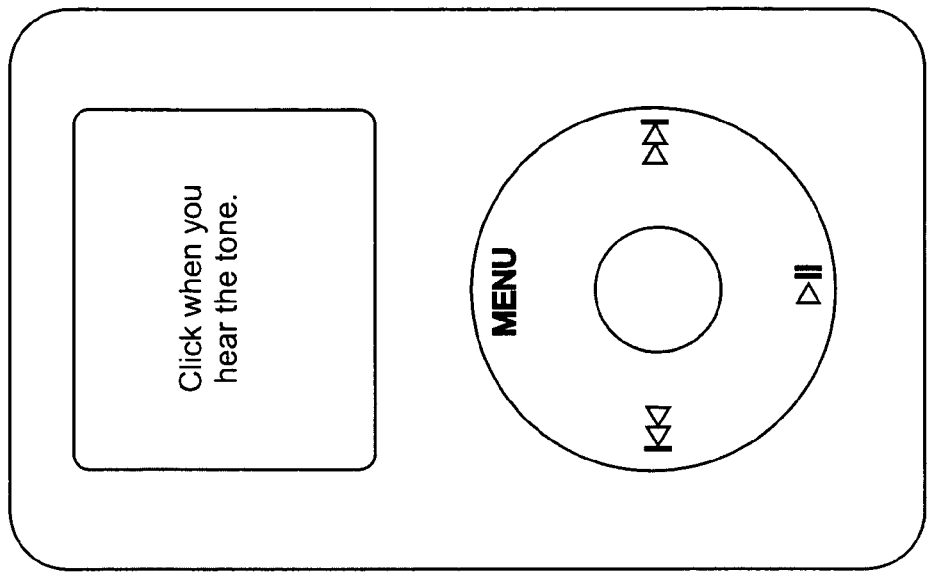
FIGS. 3 and 4 illustrate a simple control interface which may be used to implement the invention in a portable digital audio player.

The curves shown in FIG. 2 describe the hearing characteristics of a nominal "average" person. When a given individual, such as an older person, has impaired hearing which reduces that person's ability to hear sounds at particular frequencies, the hearing correction mechanism should thus give that individual a hearing response that more nearly corresponds to normal hearing. To achieve that goal, audiometric data representing the normal hearing characteristic, represented by the curve 141 in FIG. 1, are stored in the memory device 127. A procedure is then performed, as described below in conjunction with FIGS. 3-5, which captures audiological data that describes both the hearing capability of the listener and the response of the reproduction system, including room acoustics, as indicated by the dashed line curve 142 in FIG. 1. A processor then compares the normal hearing data 141 with the measured hearing capability of the listener 142 and generates and stores equalizer gain profile values as illustrated by the curve at 153 in FIG. 1. The gain vs. frequency data 153 is then used to control the response of the programmable equalizer 130 which preferentially amplifies signals at the frequencies at which the listener's hearing is impaired in comparison to normal hearing. Expressed as a formula, the equalizer gain 153 as a function of frequency, G(f), should be proportional to the difference between the normal hearing response N(f) as illustrated in FIG. 2 and the combined measured effect of the listener's hearing response M(f) and the frequency response of the reproduction equipment and room acoustics S(f). That is:

$$G(f)=N(f)-(M(f)*S(f))$$

where

G(f)=Desired equalizer gain vs. frequency where 1.0 (unity gain) means no amplification, 2.0 means amplification by 2, etc.

N(f)=Normal person's perceived amplitude vs. frequency in response to constant amplitude pressure waves over entire frequency range M(f)=Measured perceived amplitude vs. frequency of individual user in response to constant amplitude pressure waves over entire frequency range S(f)=Effective gain vs. frequency of reproduction equipment and room acoustics where 1.0 (unity gain) means the room reproduction equipment and room acoustics neither increases or decreases the amplitude at that frequency

* means the measured response M(f) is multiplied by the system gain S(f)

The present invention improves the quality of sound perceived by the listener by, in effect, administering a combined reproduction system test and an audiological hearing test to obtain data describing the combined response of the reproduction system, the room acoustics, and the listener's hearing ability over the normal audible frequency range. This testing can be automated in a variety of ways, and in many existing audio reproduction systems, can be performed by a microprocessor or digital signal processor (DSP) which is already present in the system. For example, portable music players such as the iPod® marketed by Apple Computer of Cupertino, Calif. and the Nomad® manufactured by Creative Labs, Inc. of Stillwater, OK include built-in digital processors which can be programmed to perform the necessary audiological testing, including test stimuli generation, playing and displaying instructional prompts to the listener, accepting indications from the listener indicating the listener's perception of the sounds produced by the stimuli, processing the results to create gain control values, and using those gain control values to adjust the frequency response characteristics of the device.

A simple switching device such as the pushbutton seen at 123 which can be pressed by the listener to indicate the times at which a test tones have reached a predetermined volume level, such as the threshold of hearing or a level perceived to have the same volume as that of a reference signal. The system may include stored spoken instructions seen at 137 in FIG. 2 that may be played to prompt the listener to perform certain actions. In addition, or in the alternative, the instructions may be displayed on an available display screen illustrated at 139 in FIG. 1.

Figure 3:
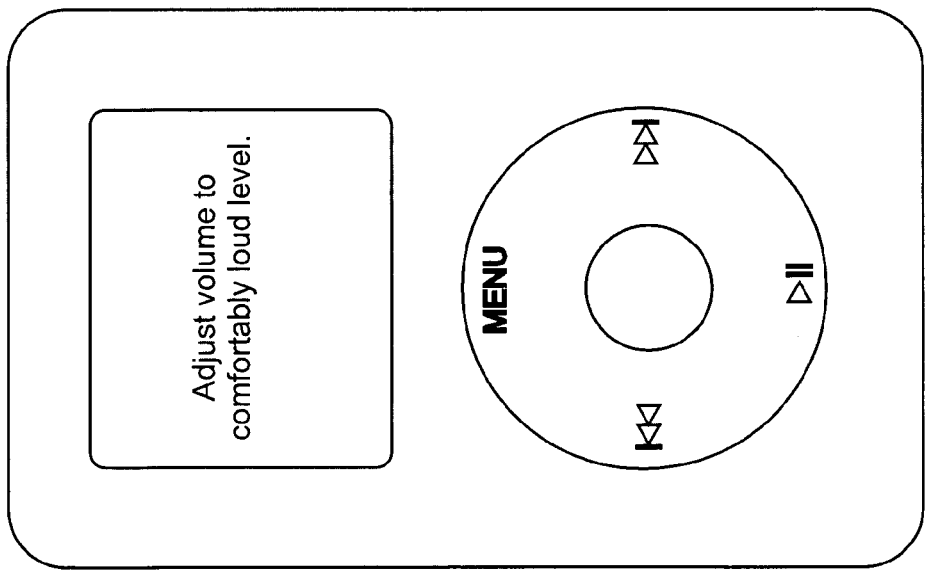

FIGS. 2 and 3 illustrate the way in which an audiological test procedure might be implemented on a portable playback device like the Apple iPod®. Using the conventional menu system provided by the device, the listener may initiate the test procedure which may begin with an audio instruction and a display illustrated in FIG. 3 requesting the user to set the device's volume setting to a comfortably load level. A sequence of different test signals (tones, spread-spectrum noise, speech, etc.) is then produced, and the listener is instructed to activate a control, such as the device's "click wheel" 401 as soon as each signal is first heard. Some or all of the test signals may be delivered to one ear at time through the headphones to separately test the hearing of each ear. In this way, the microprocessor can determine and store the listener's hearing threshold level at predetermined test frequencies across the audio spectrum for both ears.

Figure 5:
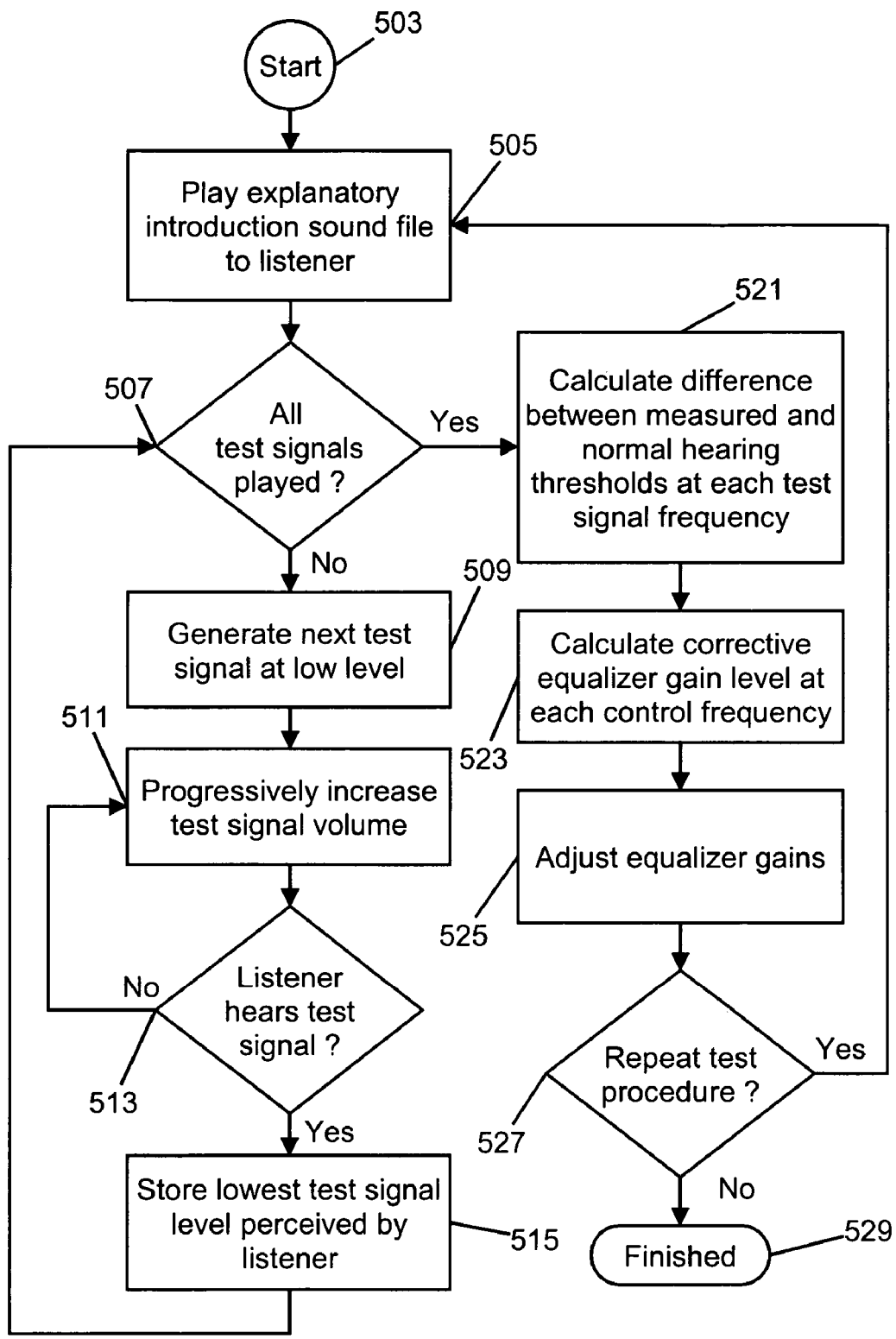
FIG. 5 is a flow chart illustrating a method for generating test signals, accepting responses, and adjusting the gain vs. frequency characteristics of a programmable equalizer to improve the performance of an audio reproduction system.

A more detailed explanation of an illustrative audiological test procedure is depicted by the flow chart seen in FIG. 5. Beginning at 503, the device first plays (or displays) introductory information to the listener explaining the procedure to be followed as indicated at 505. Then system then plays a sequence of test signal stimuli of progressively increasing volume until the last test signal has been produced as indicated by the test at 507. Each test signal has a different frequency content and begins at a low level as seen at 509. The volume of each test signal progressively increases as seen at 511 until a level is reached at which the listener first hears each signal as shown at 513. When each signal reaches the listener's hearing threshold, the user operates an input device (such as the pushbutton switch seen at 123 in FIG. 1), and the microprocessor stores a value indicative of the listener's threshold for that signal as seen at 515, and then continues with the next test signal.

When the listener's responses to all of the test stimuli have been recorded, the microprocessor compares the listener's calculated hearing threshold at each frequency with a stored value indicating the normal person's hearing threshold at that frequency (i.e. the values represented by the lowest curve in FIG. 2). After the deviation from normal hearing is determined at 521, the microprocessor calculates equalizer gain values calculated at 523 that are used at 525 to adjust the equalizer gain settings. The audible test signals produced by the generator 121 may take the form of selected tones, broadband noise, and/or narrow-band noise which is variable in frequency and amplitude. To assess hearing thresholds for speech, the generator may reproduce live voice or recorded speech at selectable calibrated levels. The same kind of test signals that are used for audiological testing by health care professionals can be used to advantage to determine the listener's hearing response.

After the equalizer has been set, the procedure may be performed again to "fine tune" the equalizer settings. Note also that two channel stereo systems and multi-channel surround sound systems may perform a separate procedure for each channel. Thus, for example, a portable music player which delivers stereo sound to two earphones may perform separate procedures for each ear. In this way, the "balance" of the reproduction is automatically adjusted so that more nearly "normal hearing" is provided to each ear, even though the two ears may be subject to different degrees of hearing impairment, or be impaired in different ways. In a multiple speaker system, such as a surround sound system, the same arrangement may be used with a separate procedure performed for each channel. Once the listener's hearing has been measured using one or more speakers, the remaining speakers may be tested to adjust their relative level (balance). Systems that employ special purpose speakers, such as a woofer, which are intended to reproduce sound only over a limited frequency range may be tested over that range only. The control settings generated for each individual listener may be separately stored so that, when a given listener desires to use the reproduction system, the listener need only identify herself and the system will then use that listener's stored equalization values.

Devices which are readily connected to a personal computer, such as portable device players which can exchange music files with a personal computer, may offload all or part of the testing procedure to the personal computer. A hearing test conducted on a personal computer or audiometer can yield audiological test data in a standard form that can then be transferred to a number of different devices to program equalizers in each device to correct for a particular person's hearing. Such audiological test data may be conveniently stored on an Internet server where it may be automatically accessed when an individual user identifies herself.

Sound reproduction systems now commonly use a digital signal processor (DSP) to digitize, compress, and decompress audio signals. These DSPs often execute equalization and filtering operations, such as Finite Impulse Response (FIR) filtering, and offer the listener graphic equalizers that can be manually adjusted to provide a desired frequency response. In such systems, the present invention may be used to automate the adjustment of such equalizers to compensate for a listener's hearing disabilities. The programmed equalization contemplated by the present invention can also be performed by the audio signal processors on a personal computer "sound card," by audio amplifiers in cellular telephones, by audio amplifiers built into stereo headphones or into "sound card" processing circuitry connected between a PC USB port and headphones, and by a wide variety of other sound processing devices which would benefit from the automatic, listener specific mechanism for compensating for differences in individual hearing abilities.

CONCLUSION

It is to be understood that the methods and apparatus which have been described above are merely illustrative applications of the principles of the invention. Numerous modifications may be made by those skilled in the art without departing from the true spirit and scope of the invention.

What is claimed is:

1. Apparatus for adjusting the frequency response characteristics of a sound reproduction system, said reproduction system including a source of audio frequency electrical signals, at least one electronic amplifier, and at least one electroacoustical transducer, said amplifier having an input connected to receive said electrical signals from said source and having an output connected to said transducer to produce sound waves corresponding to said electrical signals which are perceived by a human listener, said apparatus further comprising:

an electrical audio test signal generator connected to the input of said amplifier to produce a sequence of different test sound waves having different volume levels and different frequency content which can be heard by said listener, input means for accepting indications from said listener indicative of the perceived intensity of at least some of said different test waves as perceived by said listener, a processor responsive to said indications for translating said indications into a plurality of control values, and an adjustable equalizer connected between said source of audio frequency electrical signals and the input of said amplifier, said equalizer being coupled to said processor to receive said control values and preferentially amplify said electrical signals at different frequencies in accordance with said control values.

2. Apparatus for adjusting the frequency response characteristics of a sound reproduction system as set forth in claim 1 wherein at least selected ones of said audio test signals produced by said test signal generator have an intensity that progressively increases over time and wherein at least some of said indications from said listener indicate the time at which the sound waves produced by said selected ones of said audio test signals are first perceptible by said listener.

3. Apparatus for adjusting the frequency response characteristics of a sound reproduction system as set forth in claim 2 wherein said processor translates said times into intermediate values indicating the lowest sound level perceived by said listener at particular frequencies and wherein at least some of said control values are related to the difference between said intermediate values and the lowest sound level which is perceptible by the average person at said particular frequencies.

4. Apparatus for adjusting the frequency response characteristics of a sound reproduction system as set forth in claim 1 wherein at least some of said control values are related to the difference between the lowest sound level perceived by said listener at particular test sound frequencies and the lowest sound level which is perceptible by the average person at said test sound frequencies.

5. A method adjusting the frequency response characteristics of a sound reproduction system having an input connected to an audio signal source and an output transducer that delivers sound waves to a human listener, said method comprising, in combination, the steps of:
applying test signals having different frequency components to said input to deliver test sounds of different frequencies from said output transducer to said listener,
accepting sensory data values from said listener indicative of the listener's perception of said test sounds of different frequency,
calculating gain control values from said sensory data values, and
adjusting an equalizer connected between said input and said output transducer in accordance with said gain control values to compensate for said undesired frequency characteristics.

6. A method for adjusting the frequency response characteristics of a sound reproduction system as set forth in claim 5 wherein:
said step of applying test signals having different frequency components includes the substep of progressively increasing the volume of at least selected ones of said test signals and wherein
said step of accepting sensory data from said listener indicative of the listener's perception of said test sounds of different frequency includes the step of accepting an indication from said listener of the times when the level of said selected ones of said test signals progressively increases to a specified level as perceived by said listener.

7. A method for adjusting the frequency response characteristics of a sound reproduction system as set forth in claim 6 wherein said test signals are selected from a group comprising test tones, noise signals, and speech signals of different frequencies.

8. A method for adjusting the frequency response characteristics of a sound reproduction system as set forth in claim 6 wherein said specified level as perceived by said listener is the lowest sound level which is perceptible to said listener.

9. A method for adjusting the frequency response characteristics of a sound reproduction system as set forth in claim 8 wherein at least some of said gain control values are related to the difference between the lowest sound level perceived by said listener at particular test signal frequencies and the lowest sound level which is perceptible by the average person at said test signal frequencies.

10. A method for adjusting the frequency response characteristics of a sound reproduction system as set forth in claim 5 wherein said sound reproduction systems delivers sound via different channels to different output transducers and wherein said steps are performed separately for each of said channels.

11. An automatically programmable distortion correction system for use with an electronic sound reproduction system that includes an electronic amplifier having an input connected to an audio signal source and an output connected to an electro-acoustical transducer for delivering sound waves to a listener with impaired hearing, said programmable correction system comprising, in combination,
a test signal source coupled to said input for delivering audible test sound stimuli to said listener via said transducer,
input means for accepting one or more responses from said listener indicative of the listener's perception of said stimuli,
processing means for translating said one or more responses into measured audiological data characterizing said listener's hearing and for calculating control values from said measured audiological data, and
a programmable equalizer connected between said audio signal source and said input for preferentially amplifying the audio signal delivered to said input at different frequencies in response to said control values.

12. An automatically programmable distortion correction system as set forth in claim 11 wherein said processing means includes means for storing audiometric data indicative of the nominal frequency response characteristics of a person with normal hearing and wherein said processing means calculates said control values by comparing said measured audiological data with said audiometric data.

13. An automatically programmable distortion correction system as set forth in claim 12 wherein said audio signal is preferentially amplified to compensate for nonlinearities in the reproduction capabilities of said electronic sound reproduction system and differences between the listener's hearing response as indicated by said measured audiological data and a normal person's hearing response.

14. An automatically programmable distortion correction system as set forth in claim 11 wherein said an electronic sound reproduction system is a portable stereo audio player equipped with stereo headphones and wherein said test signal source applies separate test signals to each headphone earpiece to produce audiological data for each ear, and wherein said programmable equalizer preferentially amplifies signals differently for each stereo channel.

* * * * *